US00PP36554P2

(12) United States Plant Patent
van Swieten

(10) Patent No.: US PP36,554 P2
(45) Date of Patent: Mar. 18, 2025

(54) ***PHALAENOPSIS* PLANT NAMED 'PHA340530'**

(50) Latin Name: *Phalaenopsis hybrida*
Varietal Denomination: PHA340530

(71) Applicant: ANTHURA B.V., Bleiswijk (NL)

(72) Inventor: Martinus Nicolaas Gerardus van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 18/769,681

(22) Filed: Jul. 11, 2024

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 5/02
See application file for complete search history.

*Primary Examiner* — Kent L Bell
(74) *Attorney, Agent, or Firm* — C. Anne Whealy

(57) ABSTRACT

A new and distinct cultivar of *Phalaenopsis* plant named 'PHA340530', characterized by its relatively compact and upright plant habit; moderately vigorous to vigorous growth habit and moderate growth rate; strong flowering stems; strong leaves; freely flowering habit with typically four inflorescences developing per plant, each inflorescence with numerous flowers; white, greenish white and light yellowish green-colored flowers; and good postproduction longevity.

2 Drawing Sheets

Figure 1:
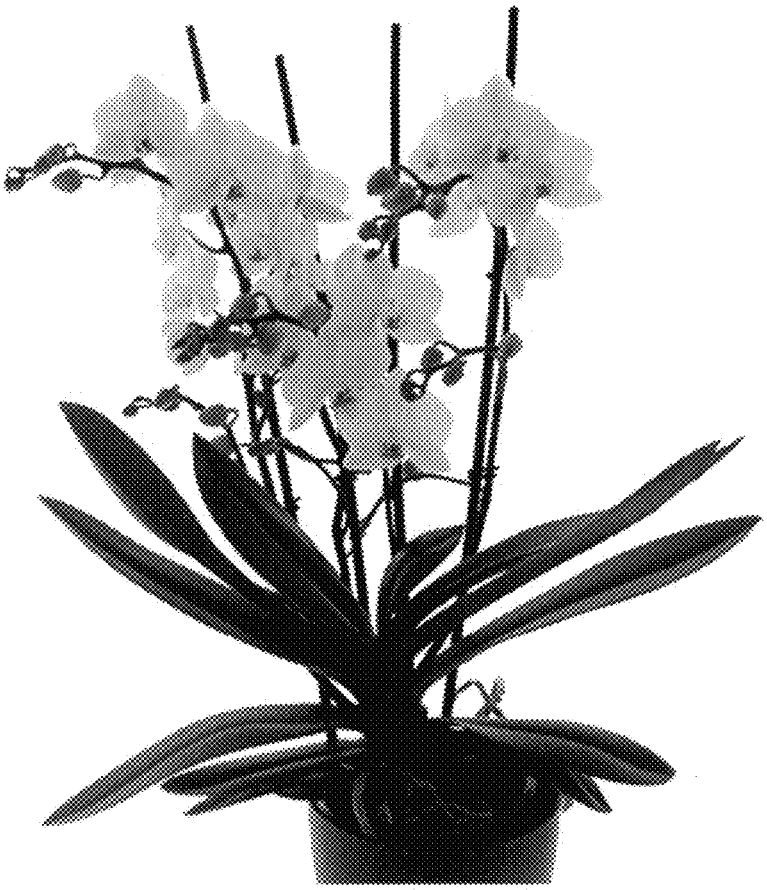

Botanical designation: *Phalaenopsis hybrida.*
Cultivar denomination: 'PHA340530'.

STATEMENT REGARDING PRIOR DISCLOSURES BY INVENTOR AND APPLICANT/ASSIGNEE

A European Community Plant Breeder's Rights application for the instant plant was filed by the Applicant/Assignee of the instant application, Anthura B.V. of Bleiswijk, The Netherlands on Jan. 22, 2023, application number 2023/0205. Foreign priority is not claimed to this application.

The Inventor and Applicant/Assignee assert that no sales, offers for sale or public distribution of the instant plant occurred more than one year prior to the effective filing date of this application.

Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosures and/or sales prior to the filing date but less than one year prior to the effective filing date.

BACKGROUND OF THE INVENTION

The present invention relates to a new and distinct cultivar of *Phalaenopsis* plant, botanically known as *Phalaenopsis hybrida*, and hereinafter referred to by the name 'PHA340530'.

The new *Phalaenopsis* plant is a product of a planned breeding program conducted by the Inventor in Bleiswijk, The Netherlands. The objective of the breeding program is to develop new compact and freely flowering *Phalaenopsis* plants with flowers with unique and attractive patterns and coloration.

The new *Phalaenopsis* plant originated from a cross-pollination in August, 2012 in Bleiswijk, The Netherlands of a proprietary selection of *Phalaenopsis hybrida* identified as code number 00001-3479, not patented, as the female, or seed, parent with a proprietary selection of *Phalaenopsis hybrida* identified as code number 30896-12, not patented, as the male, or pollen, parent. The new *Phalaenopsis* plant was discovered and selected by the Inventor as a single flowering plant from within the progeny of the stated cross-pollination grown in a controlled greenhouse environment in Bleiswijk, The Netherlands in April, 2015.

Asexual reproduction of the new *Phalaenopsis* plant by in vitro meristem propagation in a controlled environment in Bleiswijk, The Netherlands since May, 2015 has shown that the unique features of this new *Phalaenopsis* plant are stable and reproduced true to type in successive generations.

SUMMARY OF THE INVENTION

Plants of the new *Phalaenopsis* have been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'PHA340530'. These characteristics in combination distinguish 'PHA340530' as a new and distinct *Phalaenopsis* plant:

1. Relatively compact and upright plant habit.
2. Moderately vigorous to vigorous growth habit and moderate growth rate.
3. Strong flowering stems.
4. Strong leaves.
5. Freely flowering habit with typically four inflorescences developing per plant, each inflorescence with numerous flowers.

6. White, greenish white and light yellowish green-colored flowers.
7. Good postproduction longevity.

Plants of the new *Phalaenopsis* can be compared to plants of the female parent selection. Plants of the new *Phalaenopsis* differ primarily from plants of the female parent selection in leaf size as plants of the new *Phalaenopsis* have narrower leaves than plants of the female parent selection. In addition, leaves of plants of the new *Phalaenopsis* are more erect than leaves of plants of the female parent selection.

Plants of the new *Phalaenopsis* can be compared to plants of the male parent selection. Plants of the new *Phalaenopsis* differ primarily from plants of the male parent selection in sepal color as lateral sepals of plants of the new *Phalaenopsis* are greenish white and light yellowish green in color whereas lateral sepals of plants of the male parent selection are white in color. In addition, the column of plants of the new *Phalaenopsis* are white in color whereas the column of plants of the male parent selection are light yellowish green in color.

Plants of the new *Phalaenopsis* can be compared to plants of *Phalaenopsis hybrida* 'PHA312391', disclosed in U.S. Plant Pat. No. 35,786. In side-by-side comparisons, plants of the new *Phalaenopsis* differ primarily from plants of 'PHA312391' in flower size as plants of the new *Phalaenopsis* have broader flowers than plants of 'PHA312391'. In addition, leaf apices of plants of the new *Phalaenopsis* are acute whereas leaf apices of plants of 'PHA312391' are obtuse.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet (FIG. 1) is a side perspective view of a typical flowering plant of 'PHA340530' grown in a container.

Figure 2:
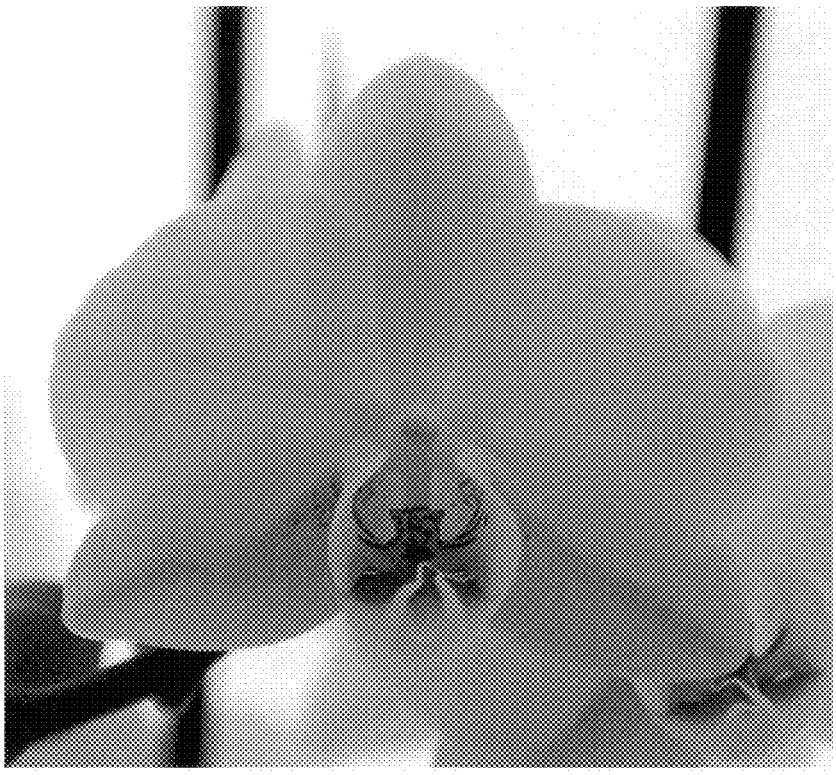

The photograph on the second sheet (FIG. 2) is a close-up view of a typical flower of 'PHA340530'.

DETAILED BOTANICAL DESCRIPTION

The aforementioned photographs and following observations and measurements describe plants grown during the late winter and early spring in 12-cm containers in a glass-covered greenhouse in Bleiswijk, The Netherlands and under cultural practices typically used in commercial *Phalaenopsis* production. Plants were 18 months old when the photographs and description were taken. During the first 14 months of production of the plants, day and night temperatures averaged 28.5° C.; and during the last four months of production of the plants, day and night temperatures averaged 20° C. Throughout the production of the plants, light levels ranged from 100 μmol to 180 μmol. In the following description, color references are made to The Royal Horticultural Society Colour Chart, 2015 Edition, except where general terms of ordinary dictionary significance are used.

Botanical classification: *Phalaenopsis hybrida* 'PHA340530'.

Parentage:

*Female, or seed, parent*.—Proprietary selection of *Phalaenopsis hybrida* identified as code number 00001-3479, not patented.

*Male, or pollen, parent*.—Proprietary selection of *Phalaenopsis hybrida* identified as code number 30896-12, not patented.

Propagation:

*Type*.—By in vitro meristem propagation.

*Time to initiate roots, summer and winter*.—About two weeks at temperatures about 28° C. to 30° C.

*Time to produce a rooted young plant, summer and winter*.—About 20 to 25 weeks at temperatures about 28° C. to 30° C.

*Root description*.—Thick, fibrous; typically light green in color; actual color of the roots is dependent on substrate composition, water quality, fertilizer, substrate temperature and age of roots.

*Rooting habit*.—Freely branching; medium density.

Plant description:

*Plant form and growth habit*.—Herbaceous epiphyte relatively compact and; upright plant habit with typically four inflorescences developing per plant, each inflorescence with numerous flowers; monopodial; moderately vigorous to vigorous growth habit and moderate growth rate.

*Plant height, substrate level to top of foliar plane*.—About 20 cm.

*Plant height, substrate level to top of floral plane*.—About 33 cm.

*Plant diameter or spread*.—About 31 cm.

Leaf description:

*Arrangement and quantity*.—Distichous, simple; sessile; about six to ten fully-developed leaves per plant.

*Length*.—About 19.7 cm.

*Width*.—About 5.2 cm.

*Aspect*.—Semi-erect.

*Shape*.—Narrowly oblong to oblanceolate; slightly carinate.

*Apex*.—Unequal acute.

*Base*.—Sheathing. Sheath length: About 1.8 cm. Sheath width: About 1.8 cm. Sheath color: Close to 143B.

*Margin*.—Entire; not undulate.

*Texture and luster, upper and lower surfaces*.—Smooth, glabrous; slightly glossy.

*Venation pattern*.—Camptodromous.

*Color*.—Developing leaves, upper surface: Close to a blend of 137B and 143A. Developing leaves, lower surface: Close to 146B; towards the margins and apex, slightly tinged with close to 200B. Fully expanded leaves, upper surface: Close to 137A and NN137B; towards the margins, close to 144A; venation, close to NN137A. Fully expanded leaves, lower surface: Close to 146B; towards the margins and apex, close to 147B; venation, close to 146A.

Inflorescence description:

*Appearance and flowering habit*.—Showy zygomorphic flowers arranged on axillary simple or branched racemes; typically four inflorescences develop per plant; each inflorescence with about 20 flowers; flowers face outwardly on outwardly arching inflorescences supported by upright peduncles; flowers with three petals, two lateral petals and one center petal transformed into a labellum and three sepals.

*Fragrance*.—None detected.

*Time to flower*.—Plants begin flowering about four months after planting; plants flower naturally during the winter into the spring.

*Flower longevity*.—Long flowering period, individual inflorescences maintain good substance for about 13 weeks on the plant; flowers not persistent.

*Inflorescence length* (*lowermost flower to inflorescence apex*).—About 24 cm.

*Inflorescence width*.—About 14.2 cm.

*Flower buds*.—Height: About 1.7 cm. Diameter: About 1.2 cm by 1.4 cm. Shape: Broadly ovate. Color: Close to 145C and 150C slightly tinged with close to 177C.

*Flower size*.—About 5 cm (vertical) by 5.7 cm (horizontal).

*Flower depth*.—About 2.4 cm.

*Petals, quantity and arrangement*.—Three, two lateral petals and one center petal transformed into a labellum.

*Lateral petals*.—Length: About 2.9 cm. Width: About 3.1 cm. Shape: Broadly deltoid-reniform to broadly deltoid-ovate. Apex: Obtuse to rounded. Margin: Entire; not undulate. Texture and luster, upper and lower surfaces: Smooth, glabrous, moderately velvety; matte. Color: When opening, upper surface: Close to 155C; towards the margins and apex, close to NN155C; at the base, close to 157A. When opening, lower surface: Close to a blend of 155C and 157D; towards the margins and apex, close to 155C; at the base, close to 145D. Fully opened, upper surface: Close to NN155D; at the base, close to 157D; color does not change with subsequent development. Fully opened, lower surface: Close to NN155D; center, slightly tinged with close to 76B; at the base, close to 157D; color does not change with subsequent development.

*Labella*.—Appearance: Three-parted with two lateral lobes and a central lobe. Length, lateral lobes: About 1.5 cm. Width, lateral lobes: About 1.2 cm. Length, central lobe: About 1.7 cm. Width, central lobe: About 5 mm to 16 mm. Length, cirrhose tips: About 9 mm. Shape, lateral lobes: Obovate. Shape, central lobe: Broadly deltoid with a slightly elongated apex. Apex, lateral lobes: Obtuse. Apex, central lobe: Cleft with two upwardly and backwardly curled cirrhose tips. Margins, lateral and central lobes: Entire. Texture and luster, lateral and central lobes, upper and lower surfaces: Smooth, glabrous, moderately velvety; matte. Callosities: Located at the base of the labellum and attachment point of the lateral petals; about 3 mm in length, about 4 mm in width and about 3 mm in height. Color: When opening, upper surface: Lateral lobes: Close to NN155D; towards the lower margins, close to 154D; at the base, axial stripes, close to 184A. Central lobe: Close to NN155C; center, close to 154C and 154D with fine dots and blotches, close to 166D; at the base, close to NN155C with radial stripes, close to 184A; cirrhose tips, close to NN155C. Callosities: Close to 4C and 4D; towards the apex, close to 11A; fine dots, close to 184B. When opening, lower surface: Lateral lobes: Close to NN155D; towards the lower margins, close to 154D. Central lobe: Close to NN155D; center, close to 154D with fine dots and blotches, close to 180A; at the base, close to 155A with radial stripes, close to 184A; cirrhose tips, close to NN155D. Fully opened, upper surface: Lateral lobes: Close to NN155D; towards the lower margins, close to 154D. Central lobe: Close to 155C; center, close to 150D with fine dots and blotches, close to 172C and 172D; at the base, close to 157C and 157D; cirrhose tips, close to 155C. Callosities: Close to 4C and 4D; towards the apex, close to 13B; fine dots, close to 184B. Fully opened, lower surface: Lateral lobes: Close to NN155D; towards the lower margins, close to 154D. Central lobe: Close to 155C; center, close to 150D with fine dots and blotches, close to 172C and 172D; at the base, close to 157C and 157D; cirrhose tips, close to 155C.

*Sepals*.—Quantity and arrangement: Three, one upper dorsal sepal and two lower lateral sepals. Length, dorsal sepal: About 3 cm. Width, dorsal sepal: About 2 cm. Length, lateral sepals: About 3.2 cm. Width, lateral sepals: About 1.9 cm. Shape, dorsal sepal: Elliptic. Shape, lateral sepals: Ovate. Apex, dorsal sepal: Obtuse to broadly and bluntly acute. Apex, lateral sepals: Bluntly acute. Base, dorsal and lateral sepals: Truncate. Margins, dorsal and lateral sepals: Entire; not undulate. Texture and luster, dorsal and lateral sepals, upper and lower surfaces: Smooth, glabrous, moderately velvety; matte. Color, dorsal sepal: When opening, upper surface: Close to 155C; at the base, close to 157A and 157B. When opening, lower surface: Close to 145C; towards the apex, close to 145C and 145D. Fully opened, upper surface: Close to NN155D; at the base, close to 157D. Fully opened, lower surface: Close to a blend of 155C and 157D; towards the margins and apex, close to NN155B; center, slightly tinged with close to 76B. Color, lateral sepals: When opening, upper surface: Upper half, close to 157C and 157D and lower half, close to 145D; towards the base, close to 145C with fine dots, close to 183C. When opening, lower surface: Upper half, close to 145D and lower half, close to 145B and 145C; main vein, close to 182B and 182C. Fully opened, upper surface: Upper half, close to 155C and lower half, close to 145D; at the base, fine dots, close to 183C. Fully opened, lower surface: Upper half, close to a blend of 155C and 157D and lower half, close to 145C; main vein, slightly tinged with close to 182C and 182D.

*Peduncles*.—Length: About 32.7 cm. Diameter: About 4 mm. Strength: Strong. Aspect: Upright to outwardly arching. Texture and luster: Smooth, glabrous; matte. Color: Close to a blend of NN137A and 148A; heavily dotted with fine dots, close to 144B.

*Pedicels*.—Length: About 2.9 cm. Diameter: About 2.5 mm. Strength: Moderately strong. Aspect: About 80° from peduncle axis. Texture and luster: Smooth, glabrous; matte. Color: Close to 146D; proximally, close to 146A and distally, close to 155C strongly tinged with close to 70D.

*Reproductive organs*.—Androecium: Column length: About 7 mm. Column width: About 4.5 mm. Column color: Close to NN155B. Pollinia quantity: Two. Pollinia diameter (per two pollinia): About 2 mm. Pollinia color: Close to 23A. Gynoecium: Stigma length: About 3 mm. Stigma width: About 4 mm. Stigma shape: Reniform. Stigma color: Close to 155C. Ovary length: About 1 cm. Ovary diameter: About 1 mm. Ovary color: Close to 149B. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate high temperatures about 40° C. and are suitable for USDA Hardiness Zones 10 to 12.

It is claimed:

1. A new and distinct *Phalaenopsis* plant named 'PHA340530' as herein illustrated and described.

* * * * *